United States Patent [19]
Atkinson et al.

[11] Patent Number: 6,162,764
[45] Date of Patent: Dec. 19, 2000

[54] PREMIXTURE COMPOSITIONS FOR APPLICATION OF PESTICIDES TO AGRICULTURAL ACREAGE

[75] Inventors: Michael Atkinson, Thornton; Randall Worthley, Greeley, both of Colo.

[73] Assignee: Platte Chemical Company, Greeley, Colo.

[21] Appl. No.: 09/323,863

[22] Filed: Jun. 1, 1999

[51] Int. Cl.$^7$ ........................................... A01N 63/00
[52] U.S. Cl. ............................................. 504/118
[58] Field of Search ............................. 504/101, 118

[56] References Cited

U.S. PATENT DOCUMENTS

| | | | |
|---|---|---|---|
| 4,714,727 | 12/1987 | Hume, III | 524/271 |
| 5,262,224 | 11/1993 | Ozaki et al. | 428/195 |

OTHER PUBLICATIONS

"Kermac 140 Flash Naphtha MSDS", Triangle Refineries, Inc., Shreveport, LA 31105, on/before Jun. 1, 1999.
"Mineral Spirits Odorless MSDS", Ashland Chemical Company, Mar. 4, 1986.
"Typical Physical Properties SAG Foam Control Compounds & Emulsions", Union Carbide, on/ before Jun. 1, 1999.
"DuoPrime Oil 70 MSDS", Lyondell Lubricants, Houston, TX 77252–2451, Apr. 4, 1994.
"Sokalan PA Polyacrylic Dispersants", BASF, on or before Jun. 10, 1999.
"Information about Silicone Antifoams—Dow Corning Antifoam a Compound, Food Grade", Dow Corning Corporation, Midland, Michigan, ©1992.
"Phosphate Esters", www.huntsman.com/products/chemcial/pch8c005.htm, May 26, 1999.
"Chevron Light Neutral Base Oil", Chevron Chemical Company, Richmond, CA, Jun. 30, 1986.
"Shell Sol 142 MT MSDS", Shell Oil Company, Houston, TX 77210, Jul. 20, 1994.
"Agricultural Oil AG 7050", Petro–Canada, Calgary, Alberta T2P 3E3, Aug. 1995.
"Sun Ag OilL 7N", Sun Refining and Marketing Company, Philadelphia, PA, May 6, 1989.
"Phosphate Esters", Witco Corporation, Houston, TX, on or before Jun. 1, 1999.
"Adjuvant Fomulations", Rhodia Company, Cranbury, NJ, on or before Jun. 1, 1999.
"Sag 47 MSDS", Osi Specialties, Inc., Greenwich, CT 06831–2559, Dec. 31, 1996.
"Exacto MSDS for Polytex A 363", Exacto, Inc., Richmond, IL 60071, Sep. 26, 1996.
"Tryfac Phosphate Esters—Technical Bulletin 163D", Emery Chemicals, May 1987.
"Stepfac 8170", Stepan Company, Northfield, IL 60093, Oct. 21, 1996.
"Good–Rite K–700 Polyacrylates", BF Goodrich Co., Cleveland, OH 44131, on or before Jun. 1, 1999.
"Anionic Surfacants–Rhodafac/ Soprophor", Rhodia Company, Cranbury, NJ, on or before 06/01/1999.

*Primary Examiner*—Shelley A. Dodson
*Assistant Examiner*—Alton Pryor
*Attorney, Agent, or Firm*—Carol W. Burton, Esq.; Hogan & Harston LLP

[57] ABSTRACT

A stable premixture composition which remains soluble or emulsifiable prior to mixing with pesticides includes an aliphatic solvent, an emulsifier, a phosphate ester water conditioner and/or a polyacrylate dispersant, an antifoam agent and a polyacrylamide drift reduction agent. A preferred formulation includes a petroleum distillate, Tallowamine, Good-Rite K-752, a silicone foam control agent, water and a polyacrylimatePolytex 363. A preferred technique for application to agricultural acreage at a rate of 10 gallons per acre, involves the addition of 3 quarts of the composition of the present invention to 200 gallons of water, followed by the addition of 3 quarts of Roundup™ or other weak acid herbicide (such as, for example, Touchdown®, 2–4,D's, sulfonyl urea, imizazolone), followed by water to 300 gallons.

18 Claims, No Drawings

PREMIXTURE COMPOSITIONS FOR APPLICATION OF PESTICIDES TO AGRICULTURAL ACREAGE

FIELD OF THE INVENTION

The present invention relates to compositions for application to agricultural acreage and application techniques relating thereto. More particularly, the present invention relates to compositions containing two or more crop treatment compounds and to application techniques in which the compounds are pre-mixed for simultaneous application to agricultural acreage.

BACKGROUND OF THE INVENTION

Liquid and solid compounds applied to agricultural crops to improve crop yield include, for example, fertilizers, pesticides (e.g., herbicides, insecticides and fungicides), surfactants, conditioning agents, drift control agents and defoamers. Many of these compounds must be separately applied due to chemical incompatibility. For example, upon mixing some compounds separate into distinct layers. Other compounds react, creating a precipitate which falls out of solution. Also by way of example, some compounds react to form a gel, solidifying in the mixing tank or fluid dispensing lines and thereby preventing application to agricultural crops.

Nonetheless, it is often desirable to mix certain compounds prior to application to agricultural crops, as individual application of each compound is necessarily more time consuming and therefore more costly and less efficient. Accordingly, sometimes two or more compounds are mixed in a tank mounted to a tractor-drawn fluid dispensing system just prior to application of the mixture to fields containing growing crops or fields in which crops are to be grown. For example, a penetrating agent, a water conditioning agent, a drift control agent, or a defoaming agent may be individually tank mixed with a pesticide for common application to agricultural acreage. However, prior to the invention disclosed herein, a premixture containing a penetrating agent, a water conditioning agent, a drift control agent and a defoaming agent was not known by the inventors of the present invention to be commercially available.

Instead, field practice typically involves the mixing of constituents to be applied to agricultural acreage in a large tank just prior to application to the agricultural acreage. More particularly, preparation of a mixture comprising a pesticide, a penetrating agent, a water conditioning agent, a drift control agent and a defoaming agent may proceed in the following way: A 300 gallon tank is filed ½ to ⅔ full with water. Thereafter, nine pints of Choice™ water conditioning agent are added, followed by 9 ounces of Fighter F™ defoaming agent, followed by 3 quarts of LI 700™ surfactant. Three quarts of Roundup™ are then added. Nine ounces of Deposit™ drift control agent are then added, after which water is added, with mixing, to fill the 300 gallon tank. The resulting mixture is conventionally applied in the field at a rate of 10 gallons per acre. It can be readily seen that the non-water, non-pesticide ingredients constitute about 7.8 quarts of the 300 gallon mixture (i.e., 3 quarts LI 700™+9 pints (=4.5 quarts) Choice™+9 ounces (about 0.15 quart) Fighter F™+9 ounces (about 0.15 quart) Deposit™.

In attempting to develop a premixture suitable for tank-mixing with certain pesticides, the following compounds were mixed: 1 quart of LI700 ™ (a penetrating surfactant), 1 quart of Choice™ (a water conditioning agent), 3 ounces of Deposit™ (a drift control agent) and 3 ounces of Fighter F™ (a defoaming agent). The resulting product was initially dark brown. Upon standing, a gel-like precipitate formed, which subsequently hardened. The product was clearly unsuitable for its intended use.

Thereafter, a premixture containing a methylated soy bean oil (a penetrating surfactant), Deposit™ drift control agent, and silicon antifoam agent in weight percents of the total premixture of 92%, 7% and 1%, respectively, was created. After mixing, a cloudy liquid formed. After standing, the lower layer hardened to a concrete-like consistency, making it completely unsuitable for its intended use.

A further attempt at creating a stable premixture resulted in a layered, although re-dispersible product, when a methylated seed oil, an emulsifier and a polyacrylamide were mixed. No antifoaming agent was used in an attempt to avoid product clouding. While this product was an improvement over the previous attempts at creating a usable premixture, the absence of an antifoam agent and the layered end product also made this product commercially unsuitable for subsequent tank mixing with pesticides. However, because the product was initially re-dispersible, a larger test batch of the premixture was made. The scaled up process resulted in a product which was susceptible to formation of chunks, requiring time-consuming filtration.

A subsequent attempt at creating a stable premixture involved the mixing of Vortex™ (96% by weight), Polytex 363 (a polyacrylamide constituting 5% by weight) and SAG 47™ defoaming agent (1% by weight). Vortex™'s primary constituents are methyl ester and AG Oil 7050. The product appeared to plug 25, 100 and 150 micron filter. Screening of the product produced numerous small chunks.

It can thus be seen that a need remains for an agricultural premixture suitable for tank mixing with a pesticide, which can condition the water to prevent precipitation of minerals in the water, serve as a drift reduction agent, and provide antifoaming and defoaming functionality, while maintaining pesticide compatibility. It is therefore against the background described above that the advances of the present invention have been made.

SUMMARY OF THE INVENTION

The present invention relates to a new composition and technique for premixing compositions prior to tank mixing with pesticides and application to agricultural acreage. The premixture composition of the present invention is stable, remaining soluble or emulsifiable prior to mixing with pesticides, and includes an aliphatic solvent, at least one emulsifier, a phosphate ester adapted for water conditioning and/or a polyacrylate dispersant, an antifoam agent and a polyacrylamide drift reduction agent. A preferred formulation includes Solvent 140™, Agricultural Oil AG 7050, L-5 Fatty Acid, NP-6, NP-10, Stepfac™ 8170, Tallowamine, Good-Rite K-752, SAG® 47 silicone foam control agent, water and Polytex 363. A preferred technique for application to agricultural acreage at a rate of 10 gallons per acre, involves the addition of 3 quarts of the composition of the present invention to 200 gallons of water, followed by the addition of 3 quarts of Roundup™ or other weak acid herbicide (such as, for example, Touchdown®, 2–4, D's, sulfonyl urea, imizazolone), followed by water to 300 gallons.

DETAILED DESCRIPTION

The present invention relates to a new composition and technique for premixing compositions prior to tank mixing with pesticides and application to agricultural acreage. The premixture composition of the present invention is stable, remaining soluble or emulsifiable prior to mixing with pesticides, and include an aliphatic solvent, at least one emulsifier, a conditioner selected from the group consisting of phosphate esters adapted for water conditioning, polyacrylate dispersants, and mixtures thereof, an antifoam agent (as used herein, the term "antifoam agent" means agents which defoam a foamy composition, prevent foaming of a composition, or both), and a polyacrylamide drift reduction agent. A preferred formulation includes Solvent 140®, Agricultural Oil AG 7050, L-5 Fatty Acid, NP-6, NP-10, Stepfac® 8170, Tallowamine, Good-Rite K-752, SAG® 47 foam control agent, water and Polytex 363 polyacrylamide. A preferred technique for application to agricultural acreage at a rate of 10 gallons per acre, involves the addition of 3 quarts of the composition of the present invention to 200 gallons of water, followed by the addition of 3 quarts of Roundup™ or other weak acid herbicide (such as, for example, Touchdown®, 2-4, D's, sulfonyl urea, imizazolone), followed by water to 300 gallons.

More generally, preferred embodiments of the compositions of the present invention specially adapted for mixing with a pesticide and application to agricultural acreage include (a) an aliphatic solvent of from approximately 50% to approximately 90% by weight of the premixture composition; (b,) an emulsifier of from approximately 5% to approximately 40% by weight of the premixture composition; (c) a conditioner at least 1% by weight of premixture composition which includes a polyacrylate dispersant of from 0% to approximately 20% by weight of the premixture composition and/or a phophate ester water conditioning agent of from 0% to approximately 15% by weight of the premixture composition; (d) water from 0% to approximately 14% by weight of the premixture composition; (e) an antifoam agent of from approximately 0.1% to approximately 10% by weight of the premixture composition; and (f) a polyacrylamide drift reduction agent of from approximately 0.5% to 15% by weight of the premixture composition. Suitable premixture compositions are those which remain either soluble or emulsifiable after manufacture, during storage and shipping, and prior to mixing with a pesticide and application to agricultural acreage.

More preferred embodiments of the compositions of the present invention include (a) an aliphatic solvent of from approximately 60% to approximately 75% by weight of the premixture composition; (b) an emulsifier of from approximately 10% to approximately 15% by weight of the premixture composition; (c) a conditioner at least 4% by weight of premixture composition which includes a polyacrylate dispersant of from 2% to approximately 5% by weight of the premixture composition and/or a phophate ester water conditioning agent of from 2% to approximately 5% by weight of the premixture composition; (d) water from 1% to approximately 5% by weight of the premixture composition; (e) an antifoam agent of from approximately 0.5% to approximately 1% by weight of the premixture composition; and (f) a polyacrylamide drift reduction agent of from approximately 1% to 5% by weight of the premixture composition. Suitable premixture compositions are those which remain either soluble or emulsifiable after manufacture, during storage and shipping, and prior to mixing with a pesticide and application to agricultural acreage.

WORKING EXAMPLE

To create a stable premixture composition, 43.31%/wt. (of the finished premixture composition) of Solvent 140™ (a mixture of C9–C12 aliphatic hydrocarbons) was mixed with 31.33%/wt. Agricultural Oil AG 7050 (severely hydrotreated paraffinic oil hydrocarbons from C15–C45). To this mixture was added 4.09%/wt. of L-5 Fatty Acid, 6.03%/wt. NP-6, 1.14%/wt. NP-10, 3.35%/wt. Stepfac® 8170, 1.00%/wt. Tallowamine, 2.35%/wt. Good-Rite K-752, 1.00%/wt. SAG® 47 silicone foam control agent available from Union Carbide, 1.40%/wt. water and 5.0%/wt. Polytex 363 polyacrylamide. The resulting premixture composition was readily emulsified and remained readily emulsifiable 24 hours after manufacture.

The above-described premixture composition was sufficiently stable to be placed in a container, sealed and shipped. It is presently recommended that 3 quarts of-his composition be added to 200 gallons of water, after which 3 quarts of Roundup™ or other weak acid herbicide (such as, for example, Touchdown®, 2-4, D's, sulfonyl urea, imizazolone) are added, with mixing. Water to 300 gallons is added, with mixing. The resulting product may be applied to agricultural acreage at a rate of 10 gallons per acre.

Preferred aliphatic solvents include are petroleum distillates (hydrotreated light) and medium aliphatic solvent naphthas. The most preferred aliphatic solvents include Solvent 140™ (a mixture of primarily c9–C12 hydrocarbons), Shell Sol 142 HT (also predominantly C9–C12 hydrocarbons whose exact composition varies) available from Shell Oil Company, Kerma 140 Flash Naphtha from Triangle Refineries, Mineral Spirits Odorless available from Ashland Chemical Company, and non-aromatic hydrocarbon solvents available from Barsol Solvents. Also preferred are mineral oils/paraffinic hydrocarbons such as those available from Petro-Canada of Calgary, Canada. Agricultural Oil AG 7050™ is a severely hydrotreated paraffinic oil of from C15–C45 hydrocarbons. Also available from Petro-Canada are HT Base Oils (hydrotreated to remove polar and aromatic compounds and impurities) such as 60 Neutral and 80 Neutral HT Base Oils. Preferred oils available from Safety Kleen include 85 Neutral™ and 70 Neutral™ both available from Safety Kleen. Also preferred are Sunspray 7N™, a solvent refined paraffinic distillate available from Sun Refining and Marketing Company, Chevron light neutral Base Oil available from Standard Oil Company of California, and Duoprime Oil 70, a white mineral oil available from Lyondell Lubricants of Houston, Tex. The suitability of these products was determined by mixing representative products with low charge anionic/nonionic polymers, medium charge anionic polymers, high charge anionic polymers, 100% defoamer compounds, 30% emulsions and 10% emulsions. Each preferred aliphatic solvent maintained solubility and/or emulsifiability with the polymers, defoamers and emulsions. In contrast, each of the vegetable oils, methyl esters, aromatic solvents, alcohols, ketones, glycols, glycol ethers and water tested was compatible with the defoamer and emulsions, but not with the polymer solutions.

A preferred phosphate ester is Stepfac® 8170 available from Stepan Company of Northfield, Ill. Stepfac® 8170 is a phosphate ester of alkyphenoxy polyethoyxethanol specifically designed for use in high electrolyte systems. Other preferred phosphate esters are anionic surfactants such as the ethoxylates available under the Rhodafac© and Sorophor™ trade names from Rhodia (formerly Rhone-Poulanc) of Cranbury, N.J. Preferred phosphate esters are also available from Witco Corporation of Greenwich, Conn., such as those having the following chemical structures:

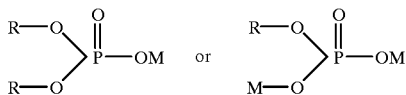

Other preferred phosphate esters are available from Emery Chemicals under their Tryfac® trademark. Tryfac® surfactants are of the following formulas:

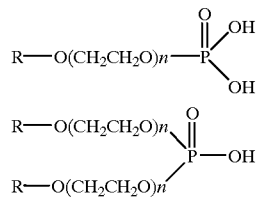

A preferred polyacrylamide is Polytex A 363 available from Exacto Inc. of Richmond, Ill. Polytex A 363 is an anionic polyacrylamide available in a water-in-oil emulsion.

A preferred polyacrylate are those of the Goodrite® K-700 polyacrylate series of acrylic acid polymers. In particular, Good-rite® K-752, having an average molecular weight of 2,100 is preferred. Also suitable are Good-rite™ K-702 (average molecular weight of 243,000), Good-rite® K-722 (average molecular weight of 104,000), and Good-rite® K-732 (average molecular weight of 5,100).

Preferred antifoam agents include SAG® silicone foam control agents available from Union Carbide, Foamex® and Rhodorsil®nonionic defoamer/antifoamers from Rhodia. More particularly, SAG® 47 is a modified polydimethylsiloxane which may be obtained from OSi Specialities, Inc. of Greenwich, Conn.

Preferred drift reduction agents include AgRho and Geronol seed and crop oil emulsifiers from Rhodia.

The premixture composition of the present invention are an easy-to-use liquid formulation suitable for use with post-emergence compounds for which a water conditioner is recommended. It is especially designed for use with weak acid herbicides such as Roundup Ultra™, Touchdown®, 2–4D, sulfonyl urea, imidazolone and the like. It reduces off-side movement of pesticide sprays, by creating uniform droplet size and holding the droplet together. It functions both to knock out existing foam and prevent solutions from foaming, thereby reducing tank filling time. In application, the volume of premixture required for effective treatment of agricultural acreage has been found to be substantially reduced over application of conventional tank premixtures.

Currently, preferred embodiments of the present invention and many improvements have been described with a degree of particularity. It should be understood that the present invention is defined by the spirit and scope of the following claims.

What is claimed is:

1. A stable premixture composition adapted for mixing with a pesticide and application to agricultural acreage comprises:
   an aliphatic solvent of from approximately 50% to approximately 90% by weight of the premixture composition;
   an emulsifier of from approximately 5% to approximately 40% by weight of the premixture composition;
   a conditioner at least 1% by weight of the premixture composition selected from the group consisting of polyacrylate dispersants of from 0% to approximately 20% by weight of the premixture composition, phosphate ester water conditioning agents of from 0% to approximately 15% by weight of the premixture composition, and mixtures thereof;
   water from 0% to approximately 14% by weight of the premixture composition;
   an antifoam agent of from approximately 0.1% to approximately 10% by weight of the premixture composition; and
   a polyacrylamide drift reduction agent of from approximately 0.5% to 15% by weight of the premixture composition, wherein the premixture composition remains either soluble or emulsifiable prior to mixing with a pesticide and application to agricultural acreage.

2. The premixture composition of claim 1, wherein the aliphatic solvent is selected from the group consisting of paraffinic hydrocarbon mixtures comprising C9–C12 hydrocarbons, white mineral oil, petroleum distillates and mixtures thereof.

3. The premixture composition of claim 1, wherein the emulsifier is selected from the group consisting of ethoxylated alkyl amine, L-5 Fatty Acid, alkylphenol polyethylene glycol ether, and mixtures thereof.

4. The premixture composition of claim 1, wherein the antifoam agent is polydimethylsiloxane.

5. The premixture composition of claim 1, wherein the phosphate ester is a phosphate ester of alkylphenoxy polyethoxyethanol.

6. The premixture composition of claim 1, wherein the aliphatic solvent is selected from the group consisting of petroleum distillates, paraffinic hydrocarbons, white mineral oil and mxitures thereof, the emulsifier is selected from the group consisting of ethoxylated alkyl amine, L-5 Fatty Acid, alkylphenolcpolyethylene glycol ether and mixtures thereof, the antifoam agent is polydimethylsiloxane, and the phosphate ester is a phosphate ester of alkylphenoxy polyethoxyethanol.

7. The premixture composition of claim 1, wherein the aliphatic solvent is from approximately 60% to approximately 75% by weight of the premixture composition, the emulsifier is from approximately 10% to approximately 15% by weight of the premixture. composition, the conditioner is at least 4% by weight of the premixture composition and includes a polyacrylate dispersant of from 2% to approximately 5% by weight of the premixture composition and a phophate ester water conditioning agent of from 2% to approximately 5% by weight of the premixture composition, water is from 1% to approximately 5% by weight of the premixture composition, the antifoam agent is from approximately 0.5% to approximately 1% by weight of the premixture composition, and the polyacrylamide drift reduction agent of from approximately 1% to 5% by weight of the premixture composition.

8. The premixture composition of claim 1, wherein the aliphatic solvent is at least 75% by weight of the premixture composition, the emulsifier is at least 13% by weight of the premixture composition, the conditioner is at least 4% by weight of the premixture composition and includes a polyacrylate dispersant of at least 2% by weight of the premixture composition and a phophate ester water conditioning agent of at least 2% of the premixture composition, water is at least 1% by weight of the premixture composition, the antifoam agent is at least 1% by weight of the premixture composition, and the polyacrylamide drift reduction agent is at least 5% by weight of the premixture composition.

9. The premixture composition of claim 8, wherein the solvent includes mineral oil.

10. A stable method of preparing a premixture composition adapted for subsequent mixture with a pesticide for application to agricultural acreage comprising the steps of:

mixing together (a) an aliphatic solvent of from approximately 50% to approximately 90% by weight of the premixture composition, (b) an emulsifier of from approximately 5% to approximately 40% by weight of the premixture composition, (c) a conditioner at least 1% by weight of premixture composition selected from the group consisting of (i) polyacrylate dispersants of from 0% to approximately 20% by weight of the premixture composition, (ii) phosphate ester water conditioning agents of from 0% to approximately 15% by weight of the premixture composition, and (iii) mixtures thereof, (d) water from 0% to approximately 14% by weight of the premixture composition, (e) an antifoam agent of from approximately 0.1% to approximately 10% by weight of the premixture composition and (f) a polyacrylamide drift reduction agent of from approximately 0.5% to 15% by weight of the premixture composition, to form a fully soluble or emulsifiable premixture composition;

placing the fully soluble or emulsifiable premixture composition in a container; and sealing the container of fully soluble or emulsifiable premixture composition, wherein the sealed container of fully soluble or emulsifiable premixture composition is adapted for transport to agricultural acreage for subsequent mixing with at least one pesticide and application to the agricultural acreage.

11. The method of claim 10, wherein the aliphatic solvent is selected from the group consisting of paraffinic hydrocarbon mixtures comprising C9–C12 hydrocarbons, white mineral oil, petroleum distillates and mixtures thereof.

12. The method of claim 1, wherein the emulsifier is selected from the group consisting of ethoxylated alkyl amine L-5 Fatty Acid, alkylphenol polyethylene glycol ether and mixtures thereof.

13. The method of claim 10, wherein the antifoam agent is is polydimethylsiloxane.

14. The method of claim 10, wherein the phosphate ester is a phosphate ester of alkylphenoxy polyethoxyethanol.

15. The method of claim 10, wherein the aliphatic solvent is selected from the group consisting of petroleum distillates, paraffinic hydrocarbons, white mineral oil and mxitures thereof, the emulsifier is selected from the group consisting of ethoxylated alkyl amine, L-5 Fatty Acid, alkylphenol polyethylene glycol ether and mixtures thereof, the antifoam agent is polydimethylsiloxane, and the phosphate ester is a phosphate ester of alkylphenoxy polyethoxyethanol.

16. The method of claim 10, wherein the aliphatic solvent is from approximately 60% to approximately 75% by weight of the premixture composition, the emulsifier is from approximately 10% to approximately 15% by weight of the premixture composition, the conditioner is at least 4% by weight of the premixture composition and includes a polyacrylate dispersant of from 2% to approximately 5% by weight of the premixture composition and a phophate ester water conditioning agent of from 2% to approximately 5% by weight of the premixture composition, water is from 1% to approximately 5% by weight of the premixture composition, the antifoam agent of from approximately 0.5% to approximately 1% by weight of the premixture composition, and the polyacrylamide drift reduction agent is from approximately 1% to 5% by weight of the premixture composition.

17. The method of claim 10, wherein the aliphatic solvent is at least 75% by weight of the premixture composition, the emulsifier is at least 13% by weight of the premixture composition, the conditioner is at least 4% by weight of the premixture composition and includes a polyacrylate dispersant of at least 2% by weight of the premixture composition and a phophate ester water conditioning agent of at least 2% of the premixture composition, water is at least 1% by weight of the premixture composition, the antifoam agent is at least 1% by weight of the premixture composition, and the polyacrylamide drift reduction agent is at least 5% by weight of the premixture composition.

18. The method of claim 10, wherein the solvent includes mineral oil.

* * * * *